United States Patent [19]

Massow et al.

[11] Patent Number: 5,194,455
[45] Date of Patent: Mar. 16, 1993

[54] ACRYLATE-BASED HOT-MELT PRESSURE-SENSITIVE ADHESIVES

[75] Inventors: Klaus Massow; Werner Karmann; Günther Kiessling, Hamburg, all of Fed. Rep. of Germany

[73] Assignee: Beiersdorf Aktiengesellschaft, Hamburg, Fed. Rep. of Germany

[21] Appl. No.: 628,239

[22] Filed: Dec. 14, 1990

[30] Foreign Application Priority Data

Dec. 21, 1989 [DE] Fed. Rep. of Germany ....... 3942232

[51] Int. Cl.$^5$ .......................... C08F 2/48; C08F 20/56; C08F 220/56; C08L 15/00
[52] U.S. Cl. ..................................... 522/152; 523/111; 428/345; 428/355
[58] Field of Search ................. 522/152; 428/345, 355; 523/111

[56] References Cited

U.S. PATENT DOCUMENTS

| | | | |
|---|---|---|---|
| 3,307,544 | 3/1967 | Gander et al. | 128/156 |
| 3,321,451 | 5/1967 | Gander | 260/79.3 |
| 3,547,950 | 12/1970 | Gander | 260/33.2 |
| 3,725,115 | 4/1973 | Christenson et al. | 522/152 |
| 3,897,295 | 7/1975 | Dowbenko et al. | 522/120 |
| 4,112,213 | 9/1978 | Waldman | 428/355 |
| 4,140,115 | 2/1979 | Schonfeld | 428/411.1 |
| 4,574,130 | 3/1986 | Potter et al. | 526/240 |
| 4,699,146 | 10/1987 | Sieverding | 522/152 |

FOREIGN PATENT DOCUMENTS

| | | |
|---|---|---|
| 0024839 | 3/1981 | European Pat. Off. . |
| 1407951 | 6/1965 | France . |
| 1168333 | 10/1969 | United Kingdom . |
| 2048274 | 12/1980 | United Kingdom . |

OTHER PUBLICATIONS

Chemical Abstracts, vol. 201, Ref. 42473m–ZA 83–7367.

*Primary Examiner*—Marion E. McCamish
*Assistant Examiner*—Susan Berman
*Attorney, Agent, or Firm*—Sprung Horn Kramer & Woods

[57] ABSTRACT

The invention relates to a process for the preparation of acrylate-based pressure-sensitive hot-melt adhesives by irradiation on a substrate, characterized in that
a) at least one acrylic monomer is copolymerized with N-tert.-butylacrylamide (TBA), wherein
b) the reaction mixture (of a) to be polymerized can additionally contain one or more ethylenically unsaturated compounds which do not belong to the group of acrylic monomers of a),
c) the resulting solid polymer is heated and is applied in a form which is capable of flowing or a liquid form to a substrate, it being possible for the compositions of steps a) to c) to contain additives and auxiliaries if appropriate, and
d) the coated substrate is irradiated with high-energy radiation.

11 Claims, No Drawings

ACRYLATE-BASED HOT-MELT PRESSURE-SENSITIVE ADHESIVES

DESCRIPTION

The invention relates to a process for the preparation of acrylate-based hot-melt pressure-sensitive adhesives by irradiation on a substrate and the hot-melt pressure-sensitive adhesives obtainable by this process.

As is known, pressure-sensitive adhesive compositions which can meet the high requirements of the users in many instances can be prepared using copolymers of acrylic acid esters. One of the particular advantages of acrylate adhesive compositions is the balanced relationship between adhesive and cohesive properties, that is to say in spite of a high resistance to shear stresses, a high detachment adhesion and good contact tackiness can be achieved.

Furthermore, polyacrylates have favourable properties under a number of environmental influences, such as, for example, UV radiation or the action of heat and moisture. This particularly applies to adhesive compositions which have been prepared by the process of solvent polymerisation, since moisture-sensitive detergents such as are in general used during emulsion polymerisation can be dispensed with in this case.

The cost- and environmental awareness which has increased in particular in recent times has resulted in the desire to produce self-adhesive articles, production of which no longer gives rise to solvents. The hot-melt pressure-sensitive application process, in which the adhesive compositions are applied in the molten state to a substrate, is suitable for this.

The difficulty in formulating hot-melt pressure-sensitive adhesives is on the one hand that they must already be capable of flowing at temperatures which are not all that high. When exposed to high temperatures, there is otherwise the risk of destruction of the adhesive due to depolymerisation or gelling.

On the other hand, the pressure-sensitive adhesive composition must have the highest possible cohesion after the coating operation, so that no residue is formed when the adhesive strips are detached from the substrate, and also so that shear strengths which allow industrial uses even at elevated temperatures can also be achieved. For a long time it has seemed hardly possible to combine these contradictory requirements, so that always only one type of property had to be given particular preference.

Thus, for example, U.S. Pat. No. 4,456,741 described non-crosslinked hot-melt pressure-sensitive adhesives in which the acrylic acid ester components were modified with styrene and N-vinylpyrrolidone. These last two monomers impart to the polymer a higher glass transition temperature and therefore a better cohesiveness at ambient temperature. However, their use in adhesive compositions is at the expense of the self-adhesive properties of tack and adhesive power, especially at low temperatures, and impair the melting properties.

Another way of arriving at systems which are capable of melting is reversible crosslinking, in which intermolecular bonds are formed via secondary valency forces. U.S. Pat. No. 4,762,888, according to which the crosslinking of polyurethane acrylates of different molecular weight takes place via hydrogen bridge bonds, may be mentioned here.

Earlier proposals, as described in U.S. Pat. No. 3,925,282, envisaged crosslinking of acrylate hot-melt pressure-sensitive adhesives containing tertiary amines with salts of organic acids and transition metals. These bonds break open under the influence of heat, so that the flowability is said to be ensured in this manner.

Attempts have moreover also been made to achieve the cohesiveness via polystyrene domains, as described, for example, in U.S. Pat. No. 4,656,213 or in EP 259,968: with this type of crosslinking, the acrylic acid esters usually employed are copolymerised with macromonomers based on polystyrene, so that acrylic polymers with grafted-on polystyrene chains are formed. Since these assemble into so-called domains because of their thermodynamic incompatibility with the acrylate parts, physical crosslinking occurs.

However, it is easy to see the essential disadvantage which reversible crosslinking has in all cases: it is not possible to prepare adhesive compositions which are resistant to shearing stresses under the influence of heat in this manner, although these are being processed to a greater extent because of the increased requirements, for example in motor vehicle or aircraft construction.

An effective route for obtaining adhesive compositions having high cohesion strength is the processing of thermoplastic systems in which, when the hot-melt pressure-sensitive coating has ended, irreversible intermolecular chemical bonds are linked up, resulting in three-dimensional networks, by means of high-energy radiation. An example of this procedure which may be mentioned is U.S. Pat. No. 3,725,115, in which copolymers of acrylate esters, vinyl acetate and small amounts of acrylic acid and diacetoneacrylamide were hardened by means of high-energy electron beams.

Attempts have furthermore been made to increase the crosslinkability of acrylate hot-melt pressure-sensitive adhesives by incorporation of double bonds, as described in DE-A-3,015,463: for this, allyl acrylate or allyl methacrylate was copolymerised with acrylic acid esters, such as 2-ethylhexyl acrylate, via the acrylic double bond, whilst the allyl grouping was said to increase the radiation yield.

A similar procedure was also followed according to U.S. Pat. No. 4,438,177: this describes the preparation of low molecular weight liquid polymers having K values of between 10 and 30, which were hardened with the aid of crosslinking agents, such as allyl (meth)acrylate or polyfunctional (meth)acrylates. The latter in particular are unstable to heat, however, and tend to gel at elevated temperatures, which greatly limits their possible use.

In all the cases described above, however, the shear strength under the influence of heat which can be achieved was low. In no case were the shear endurances at 80° C. longer than in the region of only a few hundred minutes. In the following detailed description of the new acrylate hot-melt pressure-sensitive adhesives according to the invention, adhesive compositions which had shear endurances which are several times longer under similar conditions after irradiation with relatively low doses are formulated. Copolymers obtained with diacetoneacrylamide furthermore have the disadvantage of a not always satisfactory heat stability.

The object of the invention is the preparation of acrylate-based hot-melt pressure-sensitive adhesives, that is to say pressure-sensitive acrylate adhesives, which can easily be processed from the melt and can undergo radiation crosslinking with relatively low doses, subsequently have balanced pressure-sensitive adhesion properties with both a good adhesive power and at the same time high cohesion, and are distinguished by a good shear strength.

The pressure-sensitive adhesive compositions should furthermore be suitable not only for glueings generally, for example in the industrial sector, but should also be used in the medical sector, in that, for example, they stick permanently to the skin, that is to say in a moist environment, without leading to skin irritations.

This object is achieved by a process for the preparation of acrylate-based hot-melt pressure-sensitive adhesives by irradiation on a substrate, which is characterised in that a) at least one acrylic monomer is copolymerised with N-tert.-butylacrylamide (TBA), wherein b) the reaction mixture (of a) to be polymerised can additionally contain one or more ethylenically unsaturated compounds which do not belong to the group of acrylic monomers of a), c) the resulting solid polymer is heated and is applied in a form which is capable of flowing or a liquid form to a substrate, it being possible for the compositions of steps a) to c) to contain additives and auxiliaries if appropriate, and d) the coated substrate is irradiated with high-energy radiation.

Acrylic monomers a) according to the invention are preferably alkyl esters of acrylic acid or methacrylic acid of the general formula I

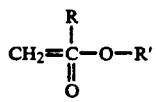

in which R is hydrogen or the methyl group and R' is a straight-chain or branched alkyl radical having 1 to 18 C atoms or a cycloalkyl radical having 3 to 18 C atoms. If only one acrylic monomer is used, the number of C atoms in its alkyl radical is preferably 4 to 8. Mixtures can contain several, for example 2 to 5, different monomers a). The content of acrylic alkyl ester a) is preferably 55 to 98% by weight, based on the total amount of monomers in the reaction mixture, particularly preferably 70 to 95% by weight and especially 70 to 90% by weight.

For use in the medical sector, for example as a plaster adhesive composition, the monomer mixtures preferably contain 80 to 95% by weight, in particular 90 to 95% by weight, of acrylic monomers.

Suitable monomers from this group are, for example, n-butyl and isobutyl acrylate and methacrylate, amyl and isoamyl acrylate, hexyl and heptyl acrylate, n-octyl, iso-octyl, 2-ethylhexyl, decyl and iso-decyl acrylate or methacrylate, and also alkyl esters, such as lauryl and stearyl acrylate or methacrylate, or cyclic alkyl esters, such as, for example, cyclohexyl or isobornyl acrylate or methacrylate.

The content of N-tert.-butylacrylamide (TBA) is preferably 2 to 30% by weight, based on the total amount of monomers in the reaction mixture, but in particular 5 to 20% by weight.

For use in the medical sector, the monomer mixtures preferably contain 5 to 20% by weight, in particular 5 to 10% by weight, of TBA.

Monomer mixtures a) of acrylic monomers and TBA containing no ethylenically unsaturated compounds b) are particularly suitable for these medical purposes. The content of TBA in these mixtures is preferably 5 to 20% by weight, in particular 5 to 10% by weight.

The reaction mixtures of a) according to the invention can furthermore optionally contain one or more, in particular 2 or 3, of the unsaturated compounds b) mentioned, which preferably carry one or more, in particular two or three, polar groups. Such mixtures are suitable for general or industrial use, or if particularly low application temperatures of the melt are required.

Preferred monomers are vinyl acetate, N-vinylpyrrolidone, N-vinylcaprolactam and monoesters and diesters of maleic acid and fumaric acid, such as, for example, monoethyl maleate, monobutyl maleate, diisopropyl maleate, dimethyl fumarate, dibutyl fumarate or dioctyl fumarate.

Monomers which contain polar groups are particularly preferred. Preferred polar groups are carboxyl groups or anhydrides thereof, carbonyl, amino, substituted amino, $C_{1-8}$-mono- or -dialkylamino, hydroxyl, $C_{1-6}$-alkoxy or halogen, for example fluorine, chlorine or bromine. Of these polar monomers, acrylic acid, methacrylic acid, crotonic acid or maleic acid or their anhydrides are particularly suitable. Maleic anhydride and maleic acid are especially preferred.

Itaconic acid and fumaric acid as well as unsaturated amides, such as, for example, acrylamide or methacrylamide, are moreover also suitable.

The content of these unsaturated compounds b) is preferably 1 to 15% by weight, but rather, so that the melt capacity is not impaired, preferably 1 to 10% by weight, based on the total amount of monomers, but in particular 1 to 5% by weight and particularly preferably 1 to 3% by weight or 1 to 2% by weight.

The adhesive compositions according to the invention can contain, if appropriate, additives and auxiliaries, such as polymerisation initiators (for example 0.05–1%), regulators (for example 10 ppm - 10%), antioxidants (for example 0.1–1%), sensitisers for UV crosslinking (for example 0.5–7%), fillers (for example 0.1–50%), resins or resin systems (for example 1–40%) or antimicrobial substances (for example 0.1–30%, preferably 1–10%), preferably in the amounts by weight mentioned, based on the total weight.

The hot-melt pressure-sensitive adhesives according to the invention can be prepared by customary polymerisation processes, such as suspension, emulsion or solvent polymerisation, polymerisation using solvents being preferred, since such adhesive compositions are free from emulsifiers, which is of advantage, for example, for sticking to the skin close to wounds. Organic solvents can moreover be removed completely from the polymer in vacuo with little expenditure on energy when the polymerisation has ended, and after condensation are available again for further polymerisations. The resulting polymer which has been freed from solvents and water is called a solid (at room temperature) polymer.

The adhesive compositions according to the invention are most easily prepared by free radical polymerisation. This technique dispenses with particular treatment of monomers and solvents, suitable initiators being organic peroxides, such as dibenzoyl peroxide, percarbonates, such as, for example, bis(4-tert.-butylcyclohexyl) peroxydicarbonate, or in particular azo compounds, such as, for example, alpha,alpha'-azoisobutyronitrile (AIBN).

Depending on the intended use, the substrate, the processing speed or particular requirements of co- or adhesion power of the hot-melt pressure-sensitive adhesive, it may be appropriate to reduce the average molecular weight of the polymer during the polymerisation. If relatively high contents of the polar comonomers mentioned under b) are present, it is also advantageous to use regulators, since this lowers the melting point or improves the flowability in the molten state. Compounds such as, for example, dodecylmercaptan, tetrabromomethane, trichlorobromomethane or alkanols, such as ethanol or isopropanol, are suitable for this purpose.

The use of N-tert.-butylacrylamide as a comonomer for the preparation of radiation-crosslinkable acrylate hot-melt pressure-sensitive adhesives does not have an adverse influence on the stability of the acrylic monomers mentioned under a) to heat and oxidation, so that particular stabilisation for the melting operation can be dispensed with. Nevertheless, it is possibly advantageous to use small amounts of antioxidants, especially if relatively high contents of the polar monomers mentioned under b) are employed or if the adhesive compositions are left at relatively high temperatures for a prolonged period of time. Suitable stabilisers are, inter alia, sterically hindered aryl thioethers, such as, for example, IRGANOX 1035® from CIBA-GEIGY (2,2'-thiodiethyl bis-(3,5-di-tert.-butyl-4-hydroxyphenyl)-propionate), or phenolic compounds, such as SANTOWHITE PC® (2,2-methylene-bis-(4-methyl-6-tert.-butylphenol)) from MONSANTO.

The content of these stabilisers should not exceed 0.50% by weight, based on the amount of polymer, and preferably even 0.30% by weight, depending on their type and the composition of the polymer. These contents ensure that the crosslinkability of the hot-melt pressure-sensitive adhesives according to the invention by high-energy ionising radiation, which is obtained by copolymerisation with the TBA, is retained in its full entirety.

The acrylate pressure-sensitive adhesive of the present invention which has been freed from the solvent can be applied to the substrates using the customary melt coating units, such as roller applicators, single- and twin-screw extruders, melt (rotary) screen printing or simple slot die applicators, the copolymer having, for example, temperatures from 60° C. to 200° C., but preferably temperatures from 80° C. to 140° C., in particular 100° to 120° C.

At relatively low temperatures, the adhesive compositions already have melt viscosities which ensure good and reliable processing, so that clear, defect-free adhesive films can in this way be applied to the most diverse substrates. As well as having a good heat resistance, they also have outstanding flow properties, so that it is possible to carry out the coating of sensitive substrates at particularly low temperatures.

Compared with the known diacetoneacrylamide copolymers, the TBA copolymers according to the invention moreover also have the advantage of a higher heat stability. The copolymer of 2-ethylhexyl acrylate and 10% by weight of diacetoneacrylamide thus already leads to a gel after exposure to the customary discharge temperature (140° C.) for four hours, whereas no tendencies of the polymer prepared with TBA to gel have yet been found.

Both firm substrates and materials in sheet or web form, preferably flexible materials, can be used as the substrate. Adhesive films and adhesive tapes for industrial or medical use, for example, are obtained in this manner.

The choice of coating materials is not restricted, and both woven and non-woven carrier materials are suitable. The non-woven carriers include, inter alia, films of polyethylene terephthalate, rigid and plasticised PVC, polyethylene and polypropylene and also metal foils. Woven substrates which can be used are textiles or cloth of, for example, wool, cotton or silk.

Carrier materials of paper, card or cellulose are likewise suitable. Foamed materials of, for example, polyurethanes or copolymers of ethylene/vinyl acetate can moreover also be coated with the acrylate-based hot-melt pressure-sensitive adhesives according to the invention.

The adhesive composition can be applied to the substrate either indirectly by the so-called transfer process, in which the adhesive composition is first applied to an auxiliary carrier with release properties and is then laminated onto the actual carrier, or directly.

The term "coating" used here is not limited to one-sided coating of carrier materials, but also includes treating substrates with the hot-melt pressure-sensitive adhesive compositions on both sides.

The hot-melt pressure-sensitive adhesives according to the invention can of course also contain fillers, such as aluminium silicate, talc, precipitated or pyrogenically obtained silicic acid, glass beads, glass fibres, carbon black, titanium dioxide, metal powders and the like; modification with various resin systems, for example terpenephenolic resins, is also possible.

The thickness of the adhesive composition layers is preferably between 5 and 1500 μm, in particular between 50 and 1000 μm, corresponding to an application rate of 5 to 1500 g/m², in particular between 5 and 1000 g/m², depending on the intended use.

For medical uses, the layer thickness is preferably 20–150 μm, in particular 20–50 μm, corresponding to an application rate of 20–150 g/m² or 20–50 g/m².

All types of high-energy and ionising radiation are suitable for crosslinking the hot-melt pressure-sensitive adhesive compositions according to the invention, such as alpha, beta, gamma and X-rays, as well as UV radiation, after addition of suitable sensitisers, for example IRGACURE® from CIBA-GEIGY (for example IRGACURE® 651, alpha,alpha-dimethoxy-alpha-phenylacetophenone) or DAROCUR® from MERCK (for example DAROCUR® 953, 1-(4-dodecylphenyl)-2-hydroxy-methylpropan-1-one).

The compositions can contain photosensitisers in amounts of preferably 0.5–7%. Hot-melt pressure-sensitive adhesive compositions crosslinked by UV radiation are preferred for the medical sector. The isotopes $Co^{60}$ and $Cs^{137}$ are usually employed as the radiation source for gamma radiation. Powerful electron accelerators have been developed for producing b-rays and are preferred for this invention. The penetration depth of these rays and therefore the maximum thickness of the coating to be crosslinked is determined by the accelerator voltage. The radiation dose absorbed was calculated from the beam current and the web speed. The functions used have been published elsewhere (W. Karmann, Coating 12/81, 365 (1981)).

The irradiation is usually carried out with exclusion of atmospheric oxygen, but this is not absolutely necessary for the result.

Doses of absorbed radiation of 5 to 250 kGy are suitable for hardening the acrylate hot-melt pressure-sensitive adhesive compositions according to the invention. A range of 5 to 100 kGy, in particular 10 to 70 kGy, is preferred because of the high crosslinking yield. Doses of 20 to 50 kGy are particularly preferred.

UV crosslinking can be carried out on the customary units by known processes. The output of the mercury vapour lamps is preferably 60–100 W/cm. At an irradiation distance of about 15 cm, the web speeds are preferably between 1 and 15 m/minute.

As shown by the increased numerical values of the Williams plasticity following the action of high-energy ionising radiation, the hot-melt pressure-sensitive adhesives obtained by copolymerisation with N-tert.-butylacrylamide are very readily crosslinkable. Hot-melt pressure-sensitive adhesives which have high shear strengths, also at elevated temperatures, are obtained by using this monomer.

The adhesive compositions have a balanced relationship between adhesive and cohesive properties, that is to say in spite of the high cohesion and interlaminar strength which can be achieved, they flow readily onto the most diverse adhesion substrates and are then distinguished by a high detachment adhesion. No residues of any type have been found on the most diverse substrates in any instance, that is to say the cohesion of the adhesive compositions obtained after irradiation was always greater than the adhesion to the substrate, although this was considerably high in some cases.

The anchoring of the hardened adhesive systems both to non-polar carriers, such as polyethylene film or polypropylene film, and to decidedly polar substrates, such as, for example, cellulose or PVC, is astonishingly good, so that in general no detachment from the usual carrier materials occurs.

The degree of crosslinking of the adhesive compositions on the substrate can be adjusted to the desired value with the aid of high-energy radiation, the use of electron beams being advantageous, the copolymerised N-tert.-butylacrylamide meaning that only relatively low radiation doses are required in order to obtain pressure-sensitive adhesive compositions having a high cohesion strength, so that these adhesive systems can also be employed for industrially demanding uses.

These hot-melt pressure-sensitive adhesive compositions have a high resistance to ageing even under the prolonged action of UV radiation or elevated temperatures: after crosslinking by irradiation, practically no further changes are found in the adhesive properties of the carrier materials coated with the acrylate hot-melt pressure-sensitive adhesives according to the invention.

As a result of the use of N-tert.-butylacrylamide (TBA) as a comonomer, the main monomers to be employed according to the invention in acrylic pressure-sensitive adhesives, such as, for example, n-butyl, hexyl, octyl and iso-octyl, 2-ethylhexyl, decyl or iso-decyl acrylate or methacrylate, retain their pressure-sensitive, self-adhesive properties. In addition, however, an increased crosslinking yield by the high-energy radiation is found, so that radiation-crosslinkable hot-melt pressure-sensitive adhesives which have an excellent cohesion and at the same time a good tack and high adhesive power can be prepared by copolymerisation of the (meth)acrylic monomers with TBA.

These properties are obtained both in a dry and in a moist environment. Hot-melt pressure-sensitive adhesive compositions prepared with N-tert.-butylacrylamide also exhibit good and permanent skin adhesion properties in the latter case, which render them suitable, inter alia, for use in the medical sector, for example for plasters, for example adhesive plasters, wound plasters, adhesive bandages, adhesive tapes, adhesive films, for example incision films, and stoma dressings. The hot-melt pressure-sensitive adhesive composition according to the invention can advantageously be provided with antimicrobial active compounds for medical purposes. The content can be about 0.1 to 30% by weight, based on the total weight. Such active compounds for self-adhesive compositions are described in the literature. The invention also relates to these uses.

Although the adhesive materials thus prepared do not require the high adhesive forces and shear strengths of industrial adhesive tapes, they offer all the advantages which are to be expected of a medical adhesive tape used for sticking to the skin. These include, in particular, the good tolerability on the skin—no irritation occurred even on more sensitive people—and adhesive properties which are not too aggressive: in spite of sitting permanently on the skin, the test strips could also be readily detached from this again without too much removal of the upper particles of the skin layer. The plasters treated with these adhesive compositions have only a very low tendency to wind over on the skin, in spite of the radiation dose used being only low.

The acrylate hot-melt pressure-sensitive adhesives according to the invention exhibit at least all the desired properties of an adhesive composition usually applied from solvents, that is to say, for example, the balance between cohesive and adhesive properties. They also offer the advantage that industrially expensive and cost-intensive drying units can be dispensed with during processing.

The substances used are known or commercially available.

Unless stated otherwise, all the amount data, contents and percentage contents are based on the weight and the total amount of monomers.

The invention also relates to materials in the form of sheets or webs having an application of a hot-melt pressure-sensitive adhesive which is obtainable by the process according to claim 1, and also to the use of these materials in the form of sheets or webs in the medical sector, and production thereof.

The invention furthermore also relates to radiation-crosslinked acrylate-based hot-melt pressure-sensitive adhesives which are obtained or are obtainable by the above process.

The abovementioned carriers in the form of a sheet or web which have been coated according to the invention can be cut into strips and wound up to rolls of adhesive tape.

The following test methods were used to evaluate the acrylate hot-melt pressure-sensitive adhesives according to the invention:

K value: (according to FIKENTSCHER)

The K value is a measure of the average size of the molecules of highly polymeric substances. To measure this value, one per cent strength (1 g/100 ml) solutions of the polymer in toluene were prepared and their kinematic viscosities were determined with the aid of a VOGELOSSAG viscometer. After standardisation to the viscosity of toluene, the relative viscosity is obtained, from which the K value can be calculated by the FIKENTSCHER method (Polymer 8/1967, 381 et seq.).

Peel strength (adhesive force, AF)

To measure the adhesive forces, test strips 19 mm wide were stuck without bubbles onto a finely ground (emery paper of FEPA grain 240) steel sheet of stainless steel and pressed on with a 2 kg rubber-covered roller at a speed of 10 m/minute. The steel sheet and the projecting end of the adhesive were then clamped into the ends of a tensile testing machine in a manner such that a take-off angle of 180° resulted. The adhesive tape was pulled off from the steel sheet at a speed of 300 mm/minute. The adhesive force is stated in N/cm.

Shear endurance (holding power, HP)

The shear endurance indicates the strength of the glueing under a load acting parallel to the glued tape. It is the time taken for a loaded adhesive tape to shear off completely from a steel sheet.

To determine the HP values, a test strip 19 mm wide is stuck onto a pretreated (see 180° detachment adhesion) steel platelet so that a glueing area of $19 \times 20$ mm$^2$ is formed. A 1 kg weight is hung on the projecting end of the adhesive tape with the aid of a clamp, so that a perpendicular tensile force of 5.15N per 1 cm tape width is transmitted.

The measurements were performed at room temperature (RT=22° C.) and in some cases also at 80° C. The unit of the shear endurance is minutes. If the values are preceded by a ">" symbol, this means that the measurements were interrupted after this time since no shear at all had yet been detected. "(K)" means cohesive fracture with residues of composition. "(A)" is the abbreviation for adhesive fracture.

Melt viscosity eta*

The flow properties of the non-crosslinked adhesive compositions in the molten state were also used, in addition to the abovementioned adhesive properties, to characterise the acrylate hot-melt pressure-sensitive adhesives according to the invention. The determination was carried out by an oscillating method with the aid of a "RHEOMETRIC DYNAMIC SPECTROMETER" (RDS).

A test temperature of 140° C., a normal force of 5% (=50 g) and an amplitude of 5% of the maximum deflection (=0.5 rad) were chosen as the constant framework conditions. The stated complex dynamic melt viscosity eta* determined here applies to a peripheral speed of w=10 rad/s, corresponding to a shear gradient of about $\gamma = 10/s$ (FließVerhalten von Stoffen und Stoffgemischen (Flow properties of substances and substance mixtures), W.-M. Kulicke, Verlag Hüthing & Weps, 1986, page 88 et seq.).

Williams plasticity (WP)

In cases of a high crosslinking yield to form a three-dimensional network, polymers show only a low plasticity and their tendency towards "cold flow" decreases. The increase in cohesion of the adhesive compositions can be quantified by comparing the Williams plasticities before and after irradiation with high-energy beams.

For the measurement, 2 g of a polymer are shaped into a sphere and after adequate temperature control are placed between the parallel plates of a Williams plastometer. The polymer sample is then subjected to a load of 5000 g at 38° C. for 14 minutes. The Williams plasticity is stated in mm, that is to say high values denote high crosslinking.

Gel value

The so-called gel value is another parameter for determination of the scope of crosslinking; this value is the content of polymer which has not dissolved after extraction in toluene at room temperature for 24 hours.

The following examples are intended to give an impression of how capable the new acrylate pressure-sensitive hot-melt adhesives are. From the large number of suitable coating substrates, the following materials were selected as being representative (Table I):

TABLE I

| Code | Carrier materials used for Examples Substrate |
|---|---|
| I | Wet non-woven of cellulose viscose 20/80, thickness; 225 μm, weight per unit area: 30 g/m$^2$. |
| II | Cellulose acetate woven fabric, thread count: longitudinal ≧66, transverse ≧25, weight per unit area: 95 g/m$^2$. |
| III | Film of polyethylene (PE), pretreated under pressure, weight per unit area: 110 g/m$^2$, thickness: 120 μm. |
| IV | 25 μm film of polyethylene terephthalate (PETP), weight per unit area: 35 g/m$^2$, provided with a preliminary coat of polyvinylidene chloride to improve adhesion. |
| V | Biaxially stretched polypropylene film, pretreated under pressure, weight per unit area: 30 g/m$^2$, thickness: 30 μm. |
| VI | Corona-pretreated foam of ethylene/vinyl acetate copolymer (EVA), bulk density: 200 kg/m$^3$. |
| VII | Polyethylene non-woven, weight per unit area: 55 g/m$^2$, thickness: 140 μm. |

In the examples described below, the substrate is coated with a slot die applicator. The adhesives are melted in a 2 kg cartridge with a heating jacket and forced onto the substrate under a pressure of 4 bar through a die which can likewise be heated.

The hot-melt pressure-sensitive adhesives according to the invention of the following examples are irradiated with an electron beam radiator of the scanner type from HIGH-VOLTAGE ENGINEERING CORP., Burlington. The accelerator voltage is 350 kV and the beam current varies between 10 and 50 mA. All the irradiations are performed under an inert gas atmosphere of N$_2$.

EXAMPLES 1–3

400 g of monomer mixture consisting of 95 parts by weight of 2-ethylhexyl acrylate (EHA) and 5 parts by weight of N-tert.-butylacrylamide and 133 g each of acetone and benzine (boiling range 60°–95° C.) are introduced into a 2 l glass reactor with an anchor stirrer, reflux condenser, thermometer and gas inlet tube. After the apparatus has been flushed with nitrogen for 30 minutes, it is heated up at a bath temperature of 75° C. 0.20 g of AIBN are added to the reaction mixture at an internal temperature of 60° C. to initiate the polymerisation. One hour after the start of the reaction, which can be detected by a high exothermicity and refluxing solvents, a further 0.20 g of AIBN are added to the batch.

The reaction time is 24 hours in total, the bath temperature being lowered from 75° to 65° C. after 4 hours. The dilutions required are carried out using the abovementioned benzine so that a final solids content of 45% is obtained. When the reaction has ended, 1.2 g of the antioxidant IRGANOX 1035 (CIBA-GEIGY) are dissolved in the polymer mixture and the solvent is then stripped off in vacuo.

The acrylate hot-melt pressure-sensitive adhesive prepared in this manner has a K value of 74 and a melt viscosity of 280 Pas. The Williams plasticities (WP) and gel contents for the various radiation doses are shown in Table II.

TABLE II

WP and gel contents for a polymer of EHA/TBA in the ratio 95/5.

| Dose [kGy] | WP [mm] | Gel content [%] |
|---|---|---|
| 0 | 1.02 | 0 |
| 30 | 1.74 | 45 |
| 50 | 1.98 | 66 |
| 70 | 2.43 | 72 |

The adhesive forces obtained for the various substrates and radiation doses are shown in Table III.

TABLE III

| Example | Substrate | Weight applied [g/m$^2$] | Dose [kGy] | Adhesive force [N/cm] |
|---|---|---|---|---|
| 1 | I | 40 | 30 | 2.50 |
| 2 | II | 90 | 50 | 2.15 |
| 3 | II | 90 | 70 | 1.90 |

EXAMPLE 4-10

The polymerisations were carried out analogously to Examples 1 to 3, with the proviso that the 2-ethylhexyl acrylate and TBA were employed in a ratio of 90 to 10 parts by weight in these examples. The Williams plasticities and gel contents before and after electron irradiation are shown in Table IV.

TABLE IV

WP and gel contents for a monomer ratio of EHA/TBA of 90/10.

| Dose [kGy] | WP [mm] | Gel value [% by weight] |
|---|---|---|
| 0 | 1.36 | 0 |
| 30 | 2.40 | 51 |
| 50 | 2.70 | 68 |
| 70 | 2.91 | 76 |

The K value of this type of hot-melt pressure-sensitive adhesive is 82 and the melt viscosity is 490 Pas. Coating was carried out at a composition temperature of 140° C. in all the examples. The adhesive forces obtained for the various substrates and crosslinking doses of Examples 4-10 are shown in Table V.

TABLE V

Adhesive forces for the hot-melt pressure-sensitive adhesive EHA/TBA = 90/10 of Examples 4 to 10.

| Example | Substrate | Weight applied [g/m$^2$] | Dose [kGy] | Adhesive force [N/cm] |
|---|---|---|---|---|
| 4 | I | 55 | 30 | 2.50 |
| 5 | III | 55 | 40 | 2.20 |
| 6 | III | 50 | 30 | 1.70 |
| 7 | III | 60 | 40 | 1.90 |
| 8 | VII | 20 | 20 | 3.00 |
| 9 | VII | 20 | 30 | 2.80 |
| 10 | VII | 20 | 50 | 2.75 |

The hot-melt pressure-sensitive adhesive composition employed in Examples 4 to 10 showed decidedly good sticking properties on the skin, which makes this monomer combination particularly suitable for plaster adhesive compositions which can be hardened by radiation or for adhesive tapes for fixing dressings: the substrates stayed on the skin well even under the action of moisture, caused no irritation and could easily be removed from the skin again, even after a prolonged sticking time, without the top layers of skin also being removed.

EXAMPLE 11-16

An adhesive composition in which the monomers 2-ethylhexyl acrylate and N-tert.-butylacrylamide were employed in a ratio of 80 to 20 parts by weight was prepared in accordance with Examples 1 to 3. The good radiation-crosslinkability is shown by the increase in Williams plasticity: whilst the non-irradiated copolymer had a WP of 1.98, this rose to 2.42 after hardening with 30 kGy and to 2.87 after irradiation with 50 kGy, and the action of an electron beam dose of 70 kGy even increased the Williams plasticity to 3.45.

The melt viscosity of this adhesive composition was 510 Pas, and the K value was determined as K=82. A polyester and polypropylene film were coated with a weight applied of 25 g/m$^2$, and an EVA foam was coated with a weight applied of 65 g/m$^2$. The coating temperature was 140° C.

The adhesive data measured for the various substrates and radiation doses are listed in Table VII.

TABLE VII

| Example | Substrate | Dose [kGy] | AF [N/cm] | Shear endurance in minutes RT | Shear endurance in minutes 80° C. |
|---|---|---|---|---|---|
| 11 | IV | 30 | 4.05 | >15000 | 30 (K) |
| 12 | IV | 50 | 3.85 | >15000 | >15000 |
| 13 | IV | 70 | 3.65 | >15000 | 600 (A) |
| 14 | V | 40 | 3.00 | >15000 | — |
| 15 | V | 50 | 2.90 | >15000 | — |
| 16 | VI | 70 | 4.90 | — | — |

Hot-melt pressure-sensitive adhesives with pronounced cohesive properties are obtained by copolymerisation of 2-ethylhexyl acrylate with 20 parts by weight of N-tert.-butylacrylamide. Hot-melt pressure-sensitive adhesive compositions which have an extremely high shear strength and with which still no shear at all is to be detected after 15000 minutes at room temperature can already be prepared with the low radiation dose of 30 kGy (Example 11). However, this high internal strength here is not at the expense of the adhesive power, adhesive forces of between 3.65 and 4.05 N/cm being obtained on PETP film, depending on the radiation dose, and adhesion values of about 3 N/cm being obtained when PP film is used.

EXAMPLE 17-19

For Examples 17 to 19, a monomer mixture was prepared from 69 parts by weight of 2-ethylhexyl acrylate, 20 parts by weight of n-butyl acrylate (BA), 10 parts by weight of N-tert.-butylacrylamide and 1 part by weight of acrylamide (AA) analogously to Examples 1 to 3. The acrylate hot-melt pressure-sensitive adhesive prepared with this monomer ratio has a K value of K=83.5, and the melt viscosity is 600 Pas. The crosslinkability of this system is again documented in Table VIII by the high values of the Williams plasticities and the gel contents after irradiation with electrons.

TABLE VIII

WP and gel contents before and after irradiation for an acrylate hot-melt pressure-sensitive adhesive consisting of EHA/BA/TBA/AA in the ratio 69/20/10/1

| Dose [kGy] | WP [mm] | Gel content [% by weight] |
|---|---|---|
| 0 | 1.82 | 0 |

TABLE VIII-continued

WP and gel contents before and after irradiation for an acrylate hot-melt pressure-sensitive adhesive consisting of EHA/BA/TBA/AA in the ratio 69/20/10/1

| Dose [kGy] | WP [mm] | Gel content [% by weight] |
| --- | --- | --- |
| 30 | 2.42 | 54 |
| 50 | 2.71 | 71 |
| 70 | 3.04 | 81 |

The melt composition was discharged onto PETP film (IV) at 140° C. with a weight applied of 20 g/m². The adhesive force and holding power values obtained after crosslinking are summarised in Table IX.

TABLE IX

Adhesive forces and shear strengths of the hot-melt pressure-sensitive adhesive of Examples 17–19.

| Example | Dose [kGy] | Adhesive force [N/cm] | Shear endurance in minutes | |
| --- | --- | --- | --- | --- |
| | | | Rt | 80° C. |
| 17 | 30 | 2.90 | 2650 (A) | 90 (K) |
| 18 | 50 | 2.80 | >20000 | >20000 |
| 19 | 70 | 2.55 | 19000 (A) | >20000 |

It is found that the optimum crosslinking dose for this hot-melt pressure-sensitive adhesive is between 30 and 70 kGy: after hardening with 50 kGy, still no shear was found by the shear strength measurements at room temperature after 20000 minutes, whilst the samples irradiated with 70 kGy on average already showed adhesive fracture after 19000 minutes. Both the 50 kGy and the kGy sample showed exceptionally high shear strengths at a temperature of 80° C.; still no shear at all was detectable in either case even after 20000 minutes.

EXAMPLE 20–22

A terpolymer prepared exclusively from acrylic acid esters and TBA was used for Examples 20 to 22. This is thus a hot-melt pressure-sensitive adhesive which contains no further modifying polar comonomer in addition to the TBA. The reaction mixture consists of 80 parts by weight of 2-ethylhexyl acrylate, 10 parts by weight of N-tert.-butylacrylamide and 10 parts by weight of isobornyl acrylate (IBOA), the preparation being carried out analogously to Examples 1 to 3. The K value of the adhesive composition is K=76, and a value of 340 Pas was determined for the melt viscosity.

In spite of quite a low Williams plasticity in the non-crosslinked state, high WP values and gel contents were again measured after electron irradiation (Table X).

TABLE X

Williams plasticities and gel contents for the acrylate hot-melt pressure-sensitive adhesive used in Examples 20–22.

| Dose [kGy] | WP [mm] | Gel content [% by weight] |
| --- | --- | --- |
| 0 | 1.29 | 0 |
| 30 | 2.17 | 48 |
| 50 | 2.55 | 66 |
| 70 | 2.73 | 75 |

The pressure-sensitive adhesive of Examples 20 to 22 which had been freed from the solvent was applied to a PETP film (substrate IV) at a temperature of 145° C. from a slot die with a weight applied of 30 g/m². After cross-linking with radiation doses of between 30 and 70 kGy, the adhesive forces and shear strengths shown by their results in Table XI were measured.

TABLE XI

Adhesive forces and shear strengths for the hot-melt pressure-sensitive adhesives of Examples 20–22.

| Example | Dose [kGy] | Adhesive force [N/cm] | HP/Rt [minutes] |
| --- | --- | --- | --- |
| 20 | 30 | 4.3 | 1670 (K) |
| 21 | 50 | 3.9 | 2260 (A) |
| 22 | 70 | 3.3 | 2325 (A) |

EXAMPLE 23–26

A polymer which contained 87 parts by weight of 2-ethylhexyl acrylate, 10 parts by weight of TBA and 3 parts by weight of acrylic acid (AAc) was used for Examples 23 to 26. The preparation procedure was as in Examples 1 to 3. To reduce the average molecular weight, 8 g of isopropanol were additionally also added to the mixture before the start of polymerisation, so that an adhesive composition having a K value of K=65 was formed. The melt viscosity was determined as 380 Pas.

The plastic properties and the crosslinkability of this system were again determined via the Williams plasticities and gel contents, the values of which are show in Table XII.

TABLE XII

Gel values and Williams plasticities of the hot-melt pressure-sensitive adhesive of Examples 23–26.

| Dose [kGy] | WP [mm] | Gel content [% by weight] |
| --- | --- | --- |
| 0 | 1.71 | 0 |
| 30 | 2.46 | 55 |
| 50 | 2.79 | 70 |
| 70 | 3.19 | 77 |

Polyester film and PP film were coated with a weight applied of 25 g/m², it being found that this monomer combination leads to a hot-melt pressure-sensitive adhesive which has a high cohesiveness even at elevated temperatures. The adhesive force and shear endurance values obtained after crosslinking with high-energy electron beams are summarised in Table XIII.

TABLE XIII

Adhesive properties of the hot-melt pressure-sensitive adhesive of Examples 23 to 26.

| Example | Substrate | Dose [kGy] | Adhesive force [N/cm] | Shear endurance | |
| --- | --- | --- | --- | --- | --- |
| | | | | RT | 80° C. |
| 23 | IV | 30 | 3.55 | >20000 | 220 (K) |
| 24 | IV | 50 | 3.45 | >20000 | >15000 |
| 25 | IV | 70 | 3.30 | >20000 | >15000 |
| 26 | V | 40 | 3.40 | >20000 | — |

These examples again show how radiation-sensitive these new hot-melt pressure-sensitive adhesives are: shear endurances of more than 20000 minutes were already found at room temperature after irradiation with 30 kGy. After hardening at from 50 kGy, still no shear at all was found even after 15000 minutes at 80° C.

EXAMPLE 27–33

The monomer mixture of the hot-melt pressure-sensitive adhesive of Examples 27 to 33 consists of 87 parts by weight of 2-ethylhexyl acrylate, 10 parts by weight of TBA and 3 parts by weight of maleic anhydride. The polymerisation was carried out analogously to Examples 1 to 3. Table XIV shows the gel values and Williams plasticities before and after irradiation.

TABLE XIV

| Dose [kGy] | Gel content [% by weight] | WP [mm] |
|---|---|---|
| 0 | 0 | 1.03 |
| 30 | 33 | 1.35 |
| 50 | 63 | 2.27 |
| 70 | 77 | 2.51 |

The K value of the hot-melt pressure-sensitive adhesive described here is K=53.7. The melt viscosity is extremely low and is only 40 Pas. An adhesive composition temperature of 90° C. was chosen for coating the substrates in these examples. In spite of the mild discharge conditions, a defect-free film of material was obtained. The results of the adhesive tests are summarised in Table XV.

TABLE XV

| Example | Substrate | Weight applied [g/m$^2$] | Dose [kGy] | Adhesive force [n/cm] | HP/Rt [minutes] |
|---|---|---|---|---|---|
| 27 | IV | 30 | 30 | 4.60 | 865 (K) |
| 28 | IV | 30 | 50 | 4.10 | 15000 (K) |
| 29 | IV | 30 | 70 | 4.00 | >20000 |
| 30 | IV | 60 | 50 | 5.20 | 9700 (A) |
| 31 | IV | 60 | 70 | 4.40 | >15000 |
| 32 | V | 30 | 40 | 3.80 | 10000 (A) |
| 33 | V | 30 | 50 | 3.80 | >15000 |

COMPARISON A and B

To demonstrate the considerable influence which the N-tert.-butylacrylamide has on the crosslinking capacity and the resulting adhesive properties. TBA-free hot-melt pressure-sensitive adhesives were prepared in Examples A and B. Whilst a 2-ethylhexyl acrylate (EHA) homopolymer was employed in Comparison A, Comparison B consisted of a copolymer of EHA and acrylic acid in a weight ratio of 99 to 1. The polymerisation was carried out analogously to Examples 1 to 3 and the K value was K=70 in both cases. Table A shows the Williams plasticities and gel contents obtained before and after irradiation.

TABLE A

Williams plasticities and gel contents of the comparison examples without TBA.

| Dose [kGy] | WP in mm | | % Gel | |
|---|---|---|---|---|
| | Comparison A | Comparison B | Comparison A | Comparison B |
| 0 | 0.81 | 0.92 | 0 | 0 |
| 30 | 1.45 | 1.96 | 20 | 52 |
| 50 | 1.50 | 2.39 | 46 | 70 |
| 70 | 2.34 | 2.43 | 56 | 75 |

The melt viscosities were determined as 260 Pas (A) and 330 Pas for comparison B. The adhesive values achieved with these comparison adhesive compositions are summarised in Table B. Polyester film (substrate IV) was coated with a weight applied of 20 g/m$^2$ (comparison A) or 28 g/m$^2$ in the case of Comparison Example B.

TABLE B

Adhesive properties of Comparison Examples A and B.

| | Dose [kGy] | Adhesive force [N/cm] | Shear endurance in minutes | |
|---|---|---|---|---|
| | | | RT | 80° C. |
| Comparison A | 30 | *) | 5 (K) | — |
| | 50 | 2.5 | 130 (K) | — |
| | 70 | 1.7 | 250 (K) | — |
| Comparison B | 30 | 2.4 | 245 (K) | 20 (K) |
| | 50 | 1.8 | 300 (K) | 90 (K) |
| | 70 | 1.4 | 200 (A) | 25 (A) |

*) The comparison composition A irradiated with 30 kGy was so incompletely crosslinked that residues of composition occurred on the steel track during the measurements of the adhesive forces.

EXAMPLE 34–36

The copolymer of 90 parts by weight of 2-ethylhexyl acrylate and 10 parts by weight of N-tert.-butylacrylamide was chosen for the UV crosslinking of Examples 34–36. The hot-melt pressure-sensitive adhesive was prepared analogously to Examples 1 to 3, but the composition was additionally also blended with 1.0% of IRGACURE 651 (Ciba-Geigy, CH), based on the solid, as a photosensitiser. The melt coating was carried out analogously to Examples 4–10 on a wet non-woven (substrate I) with a weight applied of 40 g/m$^2$.

The crosslinking was carried out by means of a mercury vapour lamp which had an output of 80 W/cm. The coated web was passed below the radiation source at a distance of 150 mm at speeds (V) of between 2 and 10 m/minute.

TABLE XVI shows the results obtained:

| Example | (V) (m/min) | WP (mm) | Gel value (% by weight) | Adhesive force (N/cm) |
|---|---|---|---|---|
| 34 | 2 | 2.61 | 65 | 2.25 |
| 35 | 5 | 2.15 | 40 | 2.55 |
| 36 | 10 | 1.78 | 20 | 3.80 |

We claim:

1. Process for the preparation of acrylate-based hot-melt pressure-sensitive adhesives by irradiation on a substrate, characterised in that
    a) at least one acrylic monomer is copolymerised with N-tert.-butylacrylamide (TBA), wherein
    b) the reaction mixture (of a) to be polymerised can additionally contain one or more ethylenically unsaturated compounds which do not belong to the group of acrylic monomers of a),
    c) the resulting solid polymer is heated and is applied in a form which is capable of flowing or a liquid form to a substrate, it being possible for the compositions of steps a) to c) to contain additives and auxiliaries if appropriate, and
    d) the coated substrate is irradiated with high-energy radiation.

2. Process according to claim 1, characterised in that the acrylic monomer a) is an alkyl ester of acrylic acid or methacrylic acid, the alkyl radical having 1 to 18 C atoms.

3. Process according to claim 1, characterised in that the content of acrylic monomers a) is 55 to 98% by weight.

4. Process according to claim 1, characterised in that the content of N-tert.-butylacrylamide is 2 to 30% by weight, based on the total amount of monomers.

5. Process according to claim 1, characterised in that the ethylenically unsaturated compounds contain polar groups.

6. Process according to claim 1, characterised in that the content of ethylenically unsaturated compounds is 1 to 15% by weight, based on the total amount of monomers contained in the mixture.

7. Process according to claim 1, characterised in that the copolymer is applied to a substrate at temperatures of 60° to 200° C.

8. Process according to claim 1, characterised in that the dose of the high-energy radiation is 5 to 250 kGy.

9. Radiation-crosslinked acrylate-based hot-melt pressure-sensitive adhesives obtained by the process according to claim 1.

10. Materials in the form of sheets or webs with an application of a hot-melt pressure-sensitive adhesive obtained by the process according to claim 1.

11. In the application to the skin of a sheet carrying a pressure-sensitive adhesive, the improvement which comprises employing as said sheet a sheet according to claim 10.

* * * * *